United States Patent [19]

Horn

[11] Patent Number: 4,465,692

[45] Date of Patent: Aug. 14, 1984

[54] SELECTIVE D-2 DOPAMINE RECEPTOR AGONIST

[75] Inventor: Alan S. Horn, Noordhorn, Netherlands

[73] Assignee: Nelson Research & Development Company, Irvine, Calif.

[21] Appl. No.: 455,197

[22] Filed: Jan. 3, 1982

[51] Int. Cl.³ ............................................. A61K 31/135
[52] U.S. Cl. ..................................................... 424/330
[58] Field of Search ......................................... 424/330

[56] References Cited

PUBLICATIONS

Hacksell et al., J. Med. Chem. 22, (1979), 1469–1475.
Sumners et al., Arch. Pharmacol. 316, (1981), 304–310.

*Primary Examiner*—Stanley J. Friedman

[57] ABSTRACT

A method of selectively stimulating D-2 dopamine receptors in humans comprising administering to a human requiring D-2 dopamine receptor stimulation, a therapeutically effective amount of 2-(N-phenylethyl-N-propylamino)-5-hydroxytetralin or a pharmaceutically acceptable salt thereof.

1 Claim, No Drawings

SELECTIVE D-2 DOPAMINE RECEPTOR AGONIST

BACKGROUND OF THE INVENTION

1. Field of the Invention

The invention relates generally to the compound 2-(N-phenylethyl-N-propylamino)-5-hydroxytetralin (PPHT). More particularly the invention relates a method of selectively stimulating D-2 dopamine receptors.

2. Background of the Prior Art

Dopamine (DA) receptors can be divided into two main classes, D-1 and D-2 (Kebabian et al., Nature 277, 93, 1979). In addition it is known that most of the behavioral and clinical effects of DA receptor agonists occur via a stimulation of the D-2 receptor sites (Schachter et al., Nature 286,57, 1980; Seeman, Pharmacol. Rev., 32, 230, 1980; Seeman, Biochem. Pharmacol. 31, 2563, 1982).

The compound 2-(N-phenylethyl-N-propylamino)-5-hydroxytetralin (PPHT)

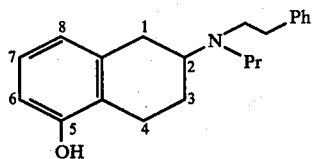

has been found to be a DA agonist in animals (Hacksell et al., J. Med. Chem. 22, 1469, 1979; Sumners et al., Arch. Pharmacol. 316, 304, 1981).

SUMMARY OF THE INVENTION

According to the present invention it has been found that the above mentioned compound, PPHT, is a potent and selective agonist of D-2 receptors. The compound is useful in the treatment of various human diseases of the central nervous system where a functional underactivity of the dopaminergic system plays a role such as in Parkinson's disease and related disorders and also disturbances of the endocrine system, e.g. hyperprolactinemia.

Prodrug esters of the phenolic group also lie within the scope of the present invention as well as pharmaceutically acceptable salts of this compound. These have the general formula:

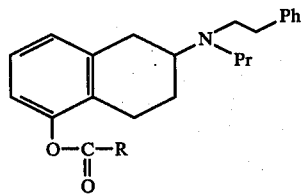

where R is methyl, ethyl, isobutyryl, pivaloyl and benzoyl. Ester prodrugs of PPHT may be prepared by treating the compound with the corresponding acid chloride (Horn et al., J. Med. Chem. 25, 993, 1982).

The acid addition salts of PPHT are prepared in the conventional manner. As acid addition salts can be used the salts derived from a therapeutically acceptable acid such as hydrochloric acid, acetic acid, propionic acid and, more particularly, from a di- or polybasic acid such as phosphoric acid, succinic acid, maleic acid, fumaric acid, citric acid, glutaric acid, citraconic acid, glutaconic acid, tartaric acid, malic acid, and ascorbic acid.

All of the above compounds of the invention contain an asymmetric carbon atom at position 2. The therapeutic properties of the compounds may to a greater or lesser degree be ascribed to either or both of the two enantiomers occurring. Thus the pure enantiomers as well as mixtures thereof are within the scope of this invention.

Thus, the invention generally relates to a method of selectively stimulating D-2 dopamine receptors in humans comprising administering to a human requiring D-2 dopamine receptor stimulation, a therapeutically effective amount of 2-(N-phenylethyl-N-propylamino)-5-hydroxytetralin or pharmaceutically acceptable salt thereof.

The invention further relates to a therapeutic composition for treating Parkinsonism comprising an effective, anti-Parkinsonism amount of the composition containing as the active ingredient 2-(N-phenylethyl-N-propylamino)-5-hydroxytetralin or a pharmaceutically acceptable salt or ester thereof.

The invention further relates to treatment of disturbances of the endocrine system such as, for example, dysfunction of prolactin synthesis (hyperprolactinemia) by inhibiting prolactin secretion.

The invention further relates to a method of treating Parkinsonism which comprises administering to a human having Parkinsonism an effective dosage of, as the active ingredient, 2-(N-phenylethyl-N-propylamino)-5-hydroxytetralin or a pharmaceutically acceptable salt or ester thereof.

A preferred embodiment of this invention is a method of treatment which comprises the administration of a therapeutically effective amount of the foregoing compounds. In general the daily dose can be from 0.05 mg./kg. to 500 mg./kg. per day and preferably from 1 mg./kg. to 250 mg./kg. per day, bearing in mind, of course, that in selecting the appropriate dosage in any specific case, consideration must be given to the patient's weight, general health, metabolism, age and other factors which influence response to the drug.

Another embodiment of this invention is the provision of pharmaceutical compositions in dosage unit form which comprise from about 1 mg. to 1 g. of a compound of the above formula.

The pharmaceutical composition may be in a form suitable for oral use, for example, as tablets, aqueous or oily suspensions, dispersible powders or granules emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with an oil medium, for example arachis oil, liquid paraffin or olive oil.

Aqueous suspensions contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents and one or more sweetening agents such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 100 mg. and about 500 mg. of the active ingredient of the formula stated above.

From the foregoing formulation discussion it is apparent that the compositions of this invention can be administered orally or parenterally. The term parenteral as used herein includes subcutaneous injection, intravenous, intramuscular, or intrasternal injection or fusion techniques.

The following examples illustrate the present invention.

EXAMPLE I

Synthesis of 2-(N-phenylethylamino)-5-hydroxytetralin (PPHT)

To a solution of 20.3 g (149 mMol) of phenylacetic acid in 100 ml of dry benzene was added 1.71 g (45 mMol) of sodium borohydride. Under an atmosphere of nitrogen the temperature was held at about 20° C. for 1 hour. To this solution was then added 1.71 g (7.8 mMol) of 2-(propylamino)-5-methoxytetralin and the mixture was refluxed for 5 hr. After cooling the benzene layer was washed with 2N NaOH (3×60 ml). The benzene layer was then extracted with 1N HCl (5×15 ml). The acid extracts were washed with ether (2×10 ml) made alkaline to litmus and then extracted with ether (4×40 ml). The ether extracts were washed with a saturated NaCL solution (2×20 ml) and after drying over $MgSO_4$ evaporated to yield an oil and refluxed for 3 hr. with 15 L ml of 48% HBr solution to yield after workup 540 mg of a white HCl salt. Recrystallization from ethanol-ether yielded an analytical sample m.p. 205°–206° C. The structure was confirmed by IR, NMR, MS and elemental analyses.

EXAMPLE II

Three in vitro test systems were used to evaluate the potency and selectivity of PPHT, i.e. the D-1 receptor in carp retina, the D-2 receptor in the intermediate lobe of the rat pituitary gland and the binding of $^3$H-spiperone to dopamine receptor containing fractions of the rat corpus striatum.

The results of the three in vitro tests are shown below in terms of "$IC_{50}$" which is the concentration of agonist required to inhibit the biochemical response by 50%.

| Compound | Intermediate lobe D-2 receptor $IC_{50}$ (uM) | Fish retina D-1 receptor $IC_{50}$ (uM) | Inhibition of spiperone bind $IC_{50}$ (nM) |
| --- | --- | --- | --- |
| PPHT | 0.04 | 3.7 | 3 |
| Dopamine | 10.0 | 10.0 | 300 |
| Apomorphine | 1.5 | 1.5 | 57 |

The results of the study show that PPHT is a very potent selective D-2 receptor agonist. That is, the foregoing studies show that PPHT is approximately 40 times more potent than the dopamine agonist apomorphine and 250 times more potent than dopamine at the D-2 receptor. Regarding selectivity, the foregoing studies show that PPHT is approximately 100 times more active at the D-2 receptor than at the D-1 receptor in contrast to dopamine and apomorphine which have the same activity at both the D-1 and D-2 receptors.

I claim:

1. A method of selectively stimulating D-2 dopamine receptors in humans comprising administering to a human requiring D-2 dopamine receptor stimulation, a therapeutically effective amount of 2-(N-phenylethyl-N-propylamino)-5-hydroxytetralin or a pharmaceutically acceptable salt or ester thereof.

* * * * *

UNITED STATES PATENT AND TRADEMARK OFFICE
CERTIFICATE OF CORRECTION

PATENT NO. : 4,465,692

DATED : August 14, 1984

INVENTOR(S) : Alan S. HORN

It is certified that error appears in the above-identified patent and that said Letters Patent are hereby corrected as shown below:

On the title page:

(22) Filing Date should read

-- January 3, 1983 --.

Signed and Sealed this

Twenty-fifth Day of December 1984

[SEAL]

Attest:

GERALD J. MOSSINGHOFF

Attesting Officer

Commissioner of Patents and Trademarks